United States Patent [19]

Ranson

[11] Patent Number: 4,560,678

[45] Date of Patent: Dec. 24, 1985

[54] NOVEL THERAPEUTIC COMPOSITION USEFUL PARTICULARLY FOR HEALING WOUNDS

[76] Inventor: Michèle Ranson, 7, place du Général, 75017 Paris, Frances

[21] Appl. No.: 549,558

[22] Filed: Nov. 7, 1983

[30] Foreign Application Priority Data

Nov. 18, 1982 [FR] France .................................. 82 19294

[51] Int. Cl.$^4$ .................... A61K 31/70; A61K 31/415; A61K 31/07
[52] U.S. Cl. ...................................... 514/44; 514/389; 514/725
[58] Field of Search ........... 424/195, 251, 253, 273 R, 424/344, DIG. 13, 180; 536/22

[56] References Cited

U.S. PATENT DOCUMENTS 3,966,967 6/1976 Lee ........................................ 424/318
4,330,527 5/1982 Arima et al. ........................... 424/94
4,347,841 9/1982 Benyó et al. .......................... 128/156

OTHER PUBLICATIONS

Merck Index, 9th Ed. 1976, No. 240.

Primary Examiner—Albert T. Meyers
Assistant Examiner—John W. Rollins, Jr.
Attorney, Agent, or Firm—Browdy and Neimark

[57] ABSTRACT

A therapeutic composition containing allantoin and desoxyribonycleic acid is useful for the healing of wounds.

12 Claims, No Drawings

NOVEL THERAPEUTIC COMPOSITION USEFUL PARTICULARLY FOR HEALING WOUNDS

FIELD OF THE INVENTION

The present invention relates to a novel therapeutic composition particularly effective in the healing of wounds.

It is an object of the present invention to provide a therapeutic composition which ensures the repair of losses of cutaneous substance, when the physiological healing process is disturbed, that is to say retarded or non-existent.

After long research (particularly clinical), Applicant has been able to perfect a composition with healing activity adapted to the treatment of wounds slow in development and difficult to heal.

GENERAL DESCRIPTION OF THE INVENTION

According to the present invention there is provided a novel therapeutic composition useful for the treatment of wounds, characterized in that it is constituted by an association of allantoin with desoxyribonucleic acid (DNA).

According to an advantageous embodiment of the invention, the ratio by weight allantoin/DNA is comprised between $\frac{1}{2}$ to $\frac{1}{8}$.

According to another advantageous embodiment of the invention, the composition comprises in addition 5,000 to 20,000 I.U. of vitamin A per 1 g of said composition.

According to another particularly advantageous embodiment, the DNA used is highly polymerized DNA.

According to the invention, the novel composition, which can be in the form of powder, gel, sterile compress ready for use, collyrium, or nasal solution, contains between 2 to 100% (weight/weight) of active principles.

Besides the foregoing features, the invention comprises yet other features which will emerge from the description which follows, referring to an example of the preparation, as well as to an clinical report.

It must, however, be well understood, that the examples and report are given purely by way of illustration of the invention of which they do not constitute, in any way a limitation thereof.

DESCRIPTION OF A PREFERRED EMBODIMENT

Example of the preparation

Into a thermostated stainless steel tank of 100 l, are introduced 35 l of distilled water heated to 65° C. Then, with stirring in small fractions are added 0.2 kg of allantoin. After total dissolution 1 kg of previously ground highly polymerized DNA is sprinkled in (average size 250 μm). It is stirred vigorously then when dissolution is complete, the volume is made up to 40 liters with distilled water heated to 65° C., then the stirring is continued for 30 minutes more.

The solution so obtained is subjected to sterile filtration and distributed in unit packaging.

Examples of Packagings Used

Compresses of woven or plaited gauze comprising 5 ml of gel for a surface area of 2.5 cm² and packaged in sterile aluminized sachets.

Dropping bottles of 5 ml for collyria.

Sterile individual tubes of useful volume 10 ml.

Sterile spraying bottles of 10 ml provided with a mechanical pump (or any suitable packaging for O.R.L.) use.

Clinical Report

The clinical experiments deal with the comparative healing action of three groups of impregnated compresses, respectively:

a 2.5% highly polymerized DNA gel (product A);
a 0.5% allantoin solution (product B)
a gel according to the present invention (2.5% of DNA and 0.5% of allantoin: product C).

The experiment was carried out on 30 patients divided into three groups of 10.

The treated population was homogeneous: it was made up of patients having ulcers of venous origin: lesions of identical size and location (diameter comprised between 1.5 and 3 cm, malleolar and plantar) the majority of the lesions developing in several weeks: 6 months for 5 cases, more than a year for two cases. The patients were distributed according to the size and the age of the lesions so as to have an equal standard in the 3 treated groups.

The general therapy was identical and limited to setting.

The treated lesions did not have considerable inflammatory characters, were little or not painful, without any sign of a distant infection, the patients being apyretic.

The treatment consisted of applying twice daily compresses largely soaked after desinfection with an antiseptic solution. The compresses left in contact with the wound were surrounded with a fine strip.

The results are collected in Table I below:

TABLE I

| Results | Compresses A | Compresses B | Compresses C |
|---|---|---|---|
| T.B. | 5 | 1 | 7 |
| B. | 2 | 1 | 2 |
| N.S. | 3 | 8 | 1 |
| Total patients | 10 | 10 | 10 |

Total number of patients treated: 30
Number of cases for each type of compress: 10
Evaluation of the results:
T.B. = complete healing;
B. = reduction in the diameter of the wound, appearance of a peripheral epidermal bead;
N.S. = no appreciable improvement.

IN CONCLUSION

In the three groups of 10 patients treated, there were obtained:

with compresses A: 5+2, namely 7 positive results;
with compresses B: only 2 positive results;
with compresses C: 9 positive results.

It is hence seen that positive effect already obtained with DNA alone (7/10) is improved if it is associated with allantoin (9/10). It is to be noted that the applications were carried out in all cases in thirty consecutive days and that healing was obtained on the average in twenty days with the composition according to the present invention. As regards to the insignificant result (N.S.), that is to say not having healing in thirty days, the treatment was extended for two additional weeks and an outline cicatrization was obtained after 30+15, namely 45 days.

The total of 9 positive results in 10, the last being on the way to healing, shows clearly the superiority of the composition according to the present invention over each of the components employed alone.

In the course of various clinical treatments, Applicant has also observed a distinct effect of the novel composition on scars, on cracks in the breast, on traumatic wounds, on buttock erythemas and on burns.

Thus, as emerges from the foregoing, the invention is in no way limited to those embodiments and uses which have just been described more explicitly; it encompasses on the contrary all modifications which may come to the spirit of the technician skilled in the art, without departing from the scope, nor the range of the present invention.

I claim:

1. A therapeutic composition useful for the treatment of wounds, constituted by an association of an amount effective to improve healing of wounds of each of allantoin and highly polymerized desoxyribonuncleic acid (DNA) and optionally a pharmaceutically acceptable carrier.

2. Composition according to claim 1, wherein the ratio by weight allantoin/DNA is comprissed between $\frac{1}{2}$ to $\frac{1}{8}$.

3. Composition according to claim 2, comprising in addition 5,000 to 20,000 I.U. of vitamin A per 1 g of said composition.

4. Composition according to claim 3, containing 2 to 100% (weight/weight) of active principles.

5. Composition according to claim 2, containing 2 to 100% (weight/weight) of active principles.

6. Composition according to claim 1, comprising in addition 5,000 to 20,000 I.U. of vitamin A per 1 g of said composition.

7. Composition according to claim 6, containing 2 to 100% (weight/weight) of active principles.

8. Composition according to claim 1, containing 2 to 100% (weight/weight) of active principles.

9. Composition according to claim 1 wherein said pharmaceutically acceptable carrier is water, and said composition is in gel form.

10. Composition according to claim 9, wherein the ratio by weight allantoin/DNA is comprised between $\frac{1}{2}$ and $\frac{1}{8}$.

11. Composition according to claim 10, comprising in addition 5 000 to 20 000 I.U. of vitamin A per 1 g of said composition.

12. Composition according to claim 9, comprising in addition 5 000 to 20 000 I.U. of vitamin A per 1 g of said composition.

* * * * *